United States Patent [19]

Boyle

[11] Patent Number: 4,957,934
[45] Date of Patent: Sep. 18, 1990

[54] 1,3-HETEROCYCLIC-SUBSTITUTED ALKANE

[75] Inventor: Francis T. Boyle, Congleton, England

[73] Assignee: Imperial Chemical Industries PLC, London, England

[21] Appl. No.: 218,255

[22] Filed: Jul. 13, 1988

[30] Foreign Application Priority Data

Jul. 15, 1987 [GB] United Kingdom ................ 8716651

[51] Int. Cl.$^5$ .................... C07D 249/08; A61K 31/41
[52] U.S. Cl. .................................... 514/383; 548/266.6
[58] Field of Search ............................ 548/262, 266.6; 514/383

[56] References Cited

U.S. PATENT DOCUMENTS 4,602,025  7/1986  Hirsch et al. ........................ 514/383

FOREIGN PATENT DOCUMENTS

| 096569 | 12/1983 | European Pat. Off. ............ 548/262 |
| 120276 | 10/1984 | European Pat. Off. . |
| 122056 | 10/1984 | European Pat. Off. . |
| 122452 | 10/1984 | European Pat. Off. ............ 548/262 |
| 165778 | 12/1985 | European Pat. Off. . |
| 165779 | 12/1985 | European Pat. Off. . |
| 166556 |  1/1986 | European Pat. Off. . |
| 178682 |  4/1986 | European Pat. Off. ............ 548/262 |
| 250198 | 12/1987 | European Pat. Off. . |

OTHER PUBLICATIONS

Taylor et al.: "Aromatase Inhibition by 5-Substituted Pyrimidines and Dihydropyrimidines", Chemical Abstracts, vol. 107, No. 11, Sep. 14, 1987, p. 688, col. 1, Abstract No. 96 674z, Columbus, Ohio.

Primary Examiner—Glennon H. Hollrah
Assistant Examiner—Patricia L. Morris
Attorney, Agent, or Firm—Cushman, Darby & Cushman

[57] ABSTRACT

A 2-propanol derivative of the formula I, wherein $R^1$ and $R^5$, which may be the same or different, are each a triazolyl, imidazolyl, pyridyl or pyrimidinyl radical; $R^2$, $R^3$ and $R^4$, which may be the same or different, are each a hydrogen atom, a 1–6C alkyl, halogenoalkyl or alkoxy radical, a 3–8C cycloalkyl radical, or a phenyl, naphthyl, phenoxy, naphthyloxy or phenyl (1–6C alkyl) radical, in each of which the aryl group optionally bears one or more substituents selected from halogen atoms, amino, carboxamido, cyano and nitro radicals, 1–6C alkyl, halogenoalkyl, alkoxy, halogenoalkoxy and alkylamino radicals, 3–8C cycloalkyl radicals, di(1–6C alkyl)amino radicals and 2–6C alkoxycarbonyl radicals; $R^6$ is a phenyl or naphthyl radical optionally bearing one or more substituents as defined above; X is a direct bond, an alkylene, alkenylene or alkynylene radical, or an oxyalkylene or thioalkylene radical wherein respectively the oxygen or sulphur atom is bonded to $R^6$ or a phenylalkylene radical in which the phenyl group bears one or more substituents as defined above for $R^6$; and Y is a hydrogen or halogen atom, a hydroxy, cyano or carbamoyl radical, or a phenyl(1–6C alkoxy) radical in which the phenyl group bears one or more substituents as defined above for $R^6$; provided that, when Y is a cyano or carbamoyl radical, neither $R^2$, $R^3$ nor $R^4$ may be an alkoxy or aryloxy radical, and either $R^2$ is a hydrogen atom, or $R^3$ and $R^4$ are both hydrogen atoms; and provided that, when $R^1$ and $R^5$ are each a 1,2,4-triazol-1-yl radical, $R^2$ is hydrogen and Y is a hydroxy radical, $R^3$ and $R^4$ may not be hydrogen or methyl when X is a direct bond, and $R^3$ and $R^4$ may not be hydrogen when X is a methylene radical; and for those compounds which contain a basic nitrogen atom, the pharmaceutically acceptable acid additon salts thereof.

9 Claims, No Drawings

1,3-HETEROCYCLIC-SUBSTITUTED ALKANE

This invention relates to heterocyclic compounds and in particular it relates to 1,3-di-heterocyclic-substituted alkane
derivatives which possess useful aromatase inhibitory activity.

Aromatase is an enzyme which effects aromatisation of ring A in the metabolic formation of various steroid hormones. Various cancers, for example breast cancer, are dependent upon circulating steroid hormones which have an aromatic ring A. Such cancers can be treated by removing the source of ring A aromatised steroid hormones, for example by the combination of oophorectomy and adrenalectomy. An alternative way of obtaining the same effect is by administering a chemical compound which inhibits the aromatisation of the steroid ring A, and the compounds of this invention are useful for this purpose.

According to the invention there is provided a heterocyclic compound of the formula I, wherein $R^1$ and $R^5$, which may be the same or different, are each a triazolyl, imidazolyl, pyridyl or pyrimidinyl radical; $R^2$, $R^3$ and $R^4$, which may be the same or different, are each a hydrogen atom, a 1-6C alkyl, halogenoalkyl or alkoxy radical, a 3-8C cycloalkyl radical, or a phenyl, naphthyl, phenoxy, naphthyloxy or phenyl(1-6C alkyl) radical, in each of which the aryl group optionally bears one or more substituents selected from halogen atoms, amino, carboxamido, cyano and nitro radicals, 1-6C alkyl, halogenoalkyl, alkoxy, halogenoalkoxy and alkylamino radicals, 3-8C cycloalkyl radicals, di(1-6C alkyl)amino radicals and 2-6C alkoxycarbonyl radicals; $R^6$ is a phenyl or naphthyl radical optionally bearing one or more substituents as defined above; X is a direct bond, an alkylene, alkenylene or alkynylene radical, or an oxyalkylene or thioalkylene radical wherein respectively the oxygen or sulphur atom is bonded to $R^6$ or a phenylalkenylene radical in which the phenyl group bears one or more substituents as defined above for $R^6$; and Y is a hydrogen or halogen atom, a hydroxy, cyano or carbamoyl radical, or a phenyl(1-6C alkoxy) radical in which the phenyl group bears one or more substituents as defined above for $R^6$; provided that, when Y is a cyano or carbamoyl radical, neither $R^2$, $R^3$ nor $R^4$ may be an alkoxy or aryloxy radical, and either $R^2$ is a hydrogen atom, or $R^3$ and $R^4$ are both hydrogen atoms; and provided that, when $R^1$ and $R^5$ are each a 1,2,4 triazol-1-yl radical, $R^2$ is hydrogen and Y is a hydroxy radical, $R^3$ and $R^4$ may not be hydrogen or methyl when X is a direct bond, and $R^3$ and $R^4$ may not be hydrogen when X is a methylene radical; and for those compounds which contain a basic nitrogen atom, the pharmaceutically acceptable acid addition salts thereof.

A suitable value for $R^1$ and $R^5$, when either is a triazolyl radical is, for example a 1,2,4 triazolyl radical, and more particularly a 1,2,4-triazol-1-yl radical.

A suitable value for $R^1$ or $R^5$ when either is an imidazolyl radical is, for example, an imidazol-1-yl radical.

A suitable value for $R^1$ or $R^5$ when either is a pyridyl radical is, for example, a pyrid-3-yl radical.

A suitable value for $R^1$ or $R^5$ when either is a pyrimidinyl radical is, for example, a pyrimidin-5 yl radical.

A suitable value for $R^2$, $R^3$ or $R^4$, when any of them is a 1-6C alkyl, halogenoalkyl or alkoxy radical, is, for example, a methyl, ethyl, propyl, isopropyl, butyl, pentyl, hexyl, trichloromethyl, difluoromethyl, trifluoromethyl, 1- or 2-chloroethyl, 2,2,2-trichloroethyl, 1- or 2-fluoroethyl, 1,1-, 1,2-or 2,2-difluoroethyl, 1,1,2-, 1,2,2- or 2,2,2-trifluoroethyl, 2,2,3,3,3-pentafluoropropyl, methoxy, ethoxy, propoxy, isopropoxy, butoxy, pentyloxy or hexyloxy radical.

A suitable value for $R^2$, $R^3$ or $R^4$, when any of them is a 3-8C cycloalkyl radical is, for example, a cyclopropyl, cyclopentyl, cyclohexyl or cyclooctyl radical.

A suitable value for $R^2$, $R^3$ or $R^4$, when any of them is a phenyl(1-6C alkyl) radical, is, for example, a benzyl, phenethyl, 1-phenylethyl, 3-phenylpropyl, 6 phenylhexyl, 1- or 2-naphthylmethyl, 1- or 2-(1- or 2-naphthyl)ethyl or 6-(1-or 2 -naphthyl)hexyl radical.

Suitable optional substituents in the aryl part of $R^2$, $R^3$, $R^4$, when any of them is an aryl, aryloxy or aralkyl radical, or in $R^6$ when it is an optionally substituted phenyl or naphthyl radical, are as defined above. Particlar such halogenoalkoxy substituents are, for example, trifluoromethoxy, 2,2,2-trichloroethoxy, 1,1-, 1,2 -and 2,2-difluoroethoxy, 1,1,2 -, 1,2,2- and 2,2,2-trifluoroethoxy, pentafluoro-ethoxy and 2,2,3,3-tetrafluoropropoxy radicals. Particular such alkylamino, dialkylamino and alkoxy-.carbonyl substituents are, for example, methylamino, ethylamino, hexylamino, dimethylamino, diethylamino, ethylmethylamino, dipropylamino, dihexylamino, methoxycarbonyl, ethoxycarbonyl, propoxycarbonyl and hexyloxycarbonyl radicals.

A suitable value for X when it is an alkylene radical is, for example, such a radical of 1 to 4 carbon atoms, which may be either straight- or branched-chain, for example a methylene, ethylene, ethylidene, propylidene, butylidene, trimethylene, tetramethylene, 1-or 2-methylethylene, 1- or 2-ethylethylene, 1-, 2- or 3-methyltrimethylene or 2-methylpropylidene radical.

A suitable value for X when it is an alkenylene radical is, for example, such a radical of 2 to 4 carbon atoms, more particularly a vinylene radical.

A suitable value for X when it is an alkynylene radical is, for example, such a radical of 2 to 4 carbon atoms, more particularly an ethynylene radical.

A suitable value for X when it is an oxyalkylene or thioalkylene radical is, for example, such a radical of from 1 or 2 carbon atoms, and more particularly an oxymethylene or thiomethylene radical.

A suitable value for X when it is phenylalkenylene radical is, for example, a benzylidene or 2 phenylethylidene radical, and suitable optional substituents therein are those defined above and particularly a cyano radical.

A suitable value for Y when it is a phenyl(1-6C alkoxy) radical is for example, a benzyloxy radical, and suitable optional substituents therein and those defined above and particularly a cyano radical.

A suitable pharmaceutically acceptable acid addition salt is, for example, a hydrochloride, nitrate, sulphate, phosphate, acetate, lactate, citrate, maleate or fumarate.

It will be understood that any one or more of four carbon atoms in the compounds of the invention may be asymmetrically substituted, so that the compound of the formula I may exist in either diastereoisomeric, racemic or optically active form. It is common general knowledge in the art how such a racemate may be separated into stereoisomers, or how such stereoisomers may be synthesized, how such diastereoisomers may be manufactured, and how their aromatase inhibitory activity may be determined.

A preferred group of compounds of the invention comprises heterocyclic compounds of the formula I wherein $R^1$ and $R^5$ are each a 1,2,4-triazolyl radical; $R^2$, $R^3$ and $R^4$ are all hydrogen atoms; X is a methylene, fluoromethylene or ethylidene radical: Y is a hydrogen or fluorine atom or a hydroxy or 4-cyanobenzyloxy radical; and $R^6$ is a phenyl radical bearing one or two substituents selected from halogen atoms and trifluoromethyl radicals and more particularly $R^6$ is a 4-chlorophenyl, 2 fluoro-4-chlorophenyl or 2-fluoro-4-trifluoromethyl radical.

A further preferred group of compounds of the invention comprises heterocyclic compounds of the formula I wherein $R^1$ and $R^5$ are each a 1,2,4-triazolyl radical; $R^2$ and $R^3$ are each a hydrogen atom; $R^4$ is a phenyl, phenoxy or benzyl radical optionally bearing a halogen or cyano substituent, and more particularly $R^4$ is a phenyl, 4-fluorophenoxy, 4 fluorobenzyl or 4-cyanobenzyl radical; and $R^6$ is a phenyl radical bearing one or two substituents selected from halogen atoms and trifluoromethyl radicals, and more particularly, $R^6$ is a 4-chlorophenyl,2,4-difluorophenyl or 2,4-difluorophenyl or 2-fluoro-4-trifluoromethylphenyl radical.

Particular preferred heterocyclic compounds of the invention are 2-(4-chlorobenzyl)-2-fluoro-1,3-di(1,2,4-triazol-1-yl)propane,2-fluoro-2-(2-fluoro 4-chlorobenzyl)1,3-di(1,2,4-triazol-1-yl)propane, 2-fluoro2-(2-fluoro-4-trifluoromethylbenzyl)1,3-di(1,2,4-triazol-1-yl)propane, 3-(4-chlorophenyl)1-(1,2,4-triazol-1-yl)2-(1,2,4-triazol-1-ylmethyl)butan2-ol, 2-(4chloro-a-fluorobenzyl)1,3-di(1,2,4-triazol01-yl)propan-2-ol, 2-(4-chlorobenzyl)-1,3-bis(1,2,4-triazol-1-yl)propane, 4[2-(4-chlorophenyl)1,3-di(1,2,4-triazol1-ylmethyl)ethoxymethyl]benzonitrile, 1-(4-fluorobenzyl)2-(2fluoro-4-trifluoromethylphenyl)-1,3-di(1,2,4-triazol1-triazol-1-yl(propan-2-ol, 2-(4-chlorophenyl)-1-(4-fluorophenoxy)-1,3-di(1,2,4-triazol-1-yl) propan-2-ol, 1-(4-cyanobenzyl)-2-(2,4-difluorophenyl)-1,3-di(1,2,4-triazol-1-yl)propan-2ol and 2-(4-chlorophenyl)1-phenyl-1,3-di(1,2,4-triazol-1-yl)propan-2-ol.

The compounds of the invention may be prepared by methods generally known for the manufacture of chemically similar compounds. Thus, the following processes are provided as further features of this invention, wherein $R^1$, $R^2$, $R^3$, $R^4$, $R^5$, $R^6$, X and Y have the meanings stated above unless otherwise stated:

(a) for those compounds wherein Y is a hydroxy radical, the reaction of an epoxide of the formula II or III, either as such or formed in situ, with a heterocyclic compound $R^1H$ or $R^5H$ respectively, or with an alkali metal salt thereof; or (b) for those compounds wherein Y is a hydroxy radical, the reaction of a halogeno compound of the formula IV, V or VI wherein Z is a halogen atom, with a heterocyclic compound $R^1H$ or $R^5H$ respectively, or with an alkali metal salt thereof; or (c) for those compounds wherein Y is a hydroxy radical, the reaction of a ketone of the formula VII or VIII with a Wittig reagent of the formula IX or X, wherein Q is a triphenylphosphine halide (Hal—.$PH_3P+$—) or dialkyl phosphite [(lower alkoxy)$_2$PO-]radical, which Wittig reagent may be preformed or formed in situ;

(d) for those compounds wherein Y is a cyano radical and X is a direct bond, the reaction of a nitrile of the formula XI or XII with a base, for example sodium hydride or n-butyl-lithium, and a halogeno compound of the formula $Z.CR^3R^4R^5$ or $R^1R^2CH.Z$ respectively, wherein Z has the meaning defined above; or (e) for those compounds wherein Y is a cyano radical, and either $R^3$ and $R^4$ are hydrogen atoms, or $R^2$ is a hydrogen atom, the reaction of a nitrile of the formula XV or XVI respectively, wherein Z' is a leaving group, for example a halogeno radical or a mesyloxy or tosyloxy radical, with a heterocyclic compound of the formula $R^5H$ or $R^1H$ respectively; or (f) for those compounds wherein Y is a hydrogen atom, the hydrogenation of an alkene derivative of the formula XVII; whereafter if desired, (i) a compound of the formula I wherein Y is a hydroxy radical and $R^1$, $R^2$, $R^3$, $R^4$, $R^5$, $R^6$ and X have any of the meanings given above, is reacted with a halogenating agent, for example diethylamino sulphur trifluoride, thionyl chloride, phosphoryl chloride, thionyl bromide or phosphoryl bromide, to form a corresponding compound of the invention wherein Y is a halogen atom; or (ii) a compound of the invention wherein Y is a cyano radical is hydrolysed with an acid, to form a corresponding compound of the invention wherein Y is a carbamoyl radical; or (iii) a compound of the invention wherein Y is a cyano radical is hydrolysed with an acid, for example concentrated sulphuric acid, for a length of time sufficient to hydrolyse the cyano group to a carboxy group, which then decarboxylates to form a corresponding compound of the invention wherein Y is a hydrogen atom; or (iv) a compound of the invention wherein Y is a halogen atom is treated with a dehalogenating agent, for example activated zinc, to form a corresponding compound of the invention wherein Y is a hydrogen atom; or (v) a compound of the invention wherein Y is a hydroxy radical is reacted with an optionally substituted phenyl(1-6C alkyl) halide in the presence of a base to form a corresponding compound of the invention wherein Y is a phenyl(1-6C alkoxy) radical.

The epoxide of the formula II, which is used as starting material in the above process (a), may be obtained by reacting an alpha-bromoketone, $R^6X.CO.CR^3R^4Br$, wherein $R^3$, $R^4$, $R^6$ and X have the meanings stated above, with a heterocyclic compound $R^5H$, or an alkali metal salt thereof, to form a compound $R^6X.CO.CR^3R^4R^5$. This product is then converted to the required epoxide II by reaction with dimethyl sulphonium methylide or dimethyl oxosulphonium methylide.

The epoxide of the formula III, which is used in the above process (a), may be obtained similarly, starting from an alpha-bromoketone $R^6X.CO.CHR^2Br$ and a heterocyclic compound $R^1H$, or an alkali metal salt thereof.

The halogeno compounds of the formulae IV and V, which are used as starting materials in the above process (b), may be obtained from the epoxides II and III respectively by reaction with the appropriate hydrogen halide, and the dihalogeno compounds VI may be obtained, for example, by reacting 1,3-dichloroacetone with a Grignard reagent $R^6XMg.Hal$, where Hal is a halogen atom.

The ketones of the formulae VII and VIII which are used as starting materials in the above process (c), may be obtained by reacting the alpha-bromoketones $R^6X.CO.CR^3R^4Br$ and $R^6X.CO.CHR^2Br$ described above, with heterocyclic compounds $R^5H$ and $R^1H$ respectively, or with an alkali metal salt thereof.

The Wittig reagents of the formulae IX and X, which are used as starting materials in the above process (c), may be obtained in conventional manner by reacting a chloromethyl heterocylic compound, $R^1CH_2Cl$ or $R^5CH_2Cl$, with either triphenylphosphine, as described in European Patent Publication No. 60222, or with potassium diethyl phosphite.

The nitrile of the formula XI, used as starting material in the above processed), may be obtained by reacting an appropriately substituted phenylacetonitrile, $R^6CH_2CN$, with a base, for example sodium hydride or n-butyl-lithium, to form the anion, which is then reacted with a halogeno compound of the formula $R^1R^2CH.Z$, as defined above, to give the required nitrile XI.

The nitrile of the formula XII, used as starting material in the above process(d), is obtained in a similar manner, using the halogeno compound of the formula $Z.CR^3R^4R_5$ in place of $R^1R^2CH.Z$.

The halogeno compound of the formula $R^1R^2CH.Z$, referred to above, may be obtained by reacting an oxo compound of the formula XIII with a compound of the formula RIH, wherein $R^1$ is a triazolyl or imidazolyl radical, or $R^1Z$ wherein Rl is a pyridyl or pyrimidinyl radical and Z has the meaning defined above, to form a carbinol of the formula XIV, which is then converted to the required halogeno compound $R^1R^2CH.Z$ by reaction with thionyl chloride, followed by basification with triethylamine.

The halogeno compound of the formula $Z.R^3R^4R^5$ is obtained similarly, starting from an oxo compound of the formula $R^3R^4$ CO and a compound $R^5H$, in which $R^5$ is triazolyl or imidazolyl radical, or R5Z, in which $R^5$ is a pyridyl or pyrimidinyl radical and Z has the meaning stated above.

The nitrile of the formula XV, used as starting material in the above process (e), may be obtained by reacting a halogeno compound of the formula XVII, wherein Z has the meaning defined above, with ethyl cyanoacetate in the presence of a base, to form a cyanoester XIX, which is treated with a base to form the anion, which in turn is then reacted with a halogeno compound of the formula $R^1R^2CHZ$, as defined above, to form a cyanoester XX. The cyanoester XX is reduced, for example with lithium borohydride, to the corresponding alcohol XXI, which is then either halogenated to form the nitrile XV wherein Z is a halogen, or reacted with the appropriate sulphonyl chloride to form the nitrile XV wherein Z is a mesyloxy or tosyloxy radical.

The nitrile of the formula XVI, used as starting material in the above process(e), is obtained similarly, using the halogeno compound $Z.CR^3R^4R^5$ in place of $R^1R^2CH.Z$.

As indicated above, the compounds of the invention are useful as aromatase inhibitors. Aromatase inhibition may be demostrated by the following tests:

DEMONSTRATION OF ACTIVITY IN VITRO

Aromatase inhibitory activity was measured using the enzyme present in the microsomal fraction of human term placenta, as described by Ryan, J. Biol, Chem. 234,268,1959. Enzyme activity was determined by measuring the amount of tritiated water released from 0.5 micromolar $(1\beta, 2\beta\text{-}^3H)$testosterone after 20 minutes incubation at 37°. The method used was essentially that described by Thomson and Siiteri, J. Biol.Chem. 249,5364,1974 except that testosterone was used in place of androstenedione. Test compounds were dissolved in dimethylsulphoxide (DMSO) to achieve final concentrations of 2, 0.2 or 0.02 µg/ml. The reaction was started by the addition of 50µl of microsome suspension to 50pl of a solution containing substrate (testosterone) and cofactors (NADPH glucose-6-phosphate and glucose-6-phosphate dehydrogenase) and either DMSO alone or a DMSO solution of test compound. Each concentration of test compound was tested in triplicate. The reaction was stopped by the addition of 200µl of a 5% (w,v) suspension of charcoal in 0.5% (w/v) solution of Dextran T70 in water. After 1 hour the charcoal was precipitated by centrifugation and 150µl of supernatant removed and the amount of tritiated water present determined using a liquid scintillation counter. The number of counts in supernatant from incubations containing test compound expressed as a percentage of the counts in supernatant from incubations containing only DMSO was taken as the degree of enzyme inhibition achieved by the test compound.

DEMONSTRATION OF ACTIVITY IN VIVO

Activity in vivo was demonstrated in terms of ovulation inhibition in female rats. Daily vaginal smears were taken from rats housed under controlled lighting (lights on 06.00 hr to 20.00 hr) and those having a vaginal smear pattern consistent with 4-day ovarian cycles were selected. To these rats a single dose of test compound was given either at 16.00 hr on Day 2 of the cycle or at 12.00 hr on Day 3 of the cycle. The rats were then killed in the morning following Day 4 of the cycle—approximately 64 hours after Day 2 treatments or approximately 46 hours after Day 3 treatments—and the presence or absence of eggs in the fallopian tubes determined. The presence of eggs indicates that the rats have ovulated.

Without treatment more than 95% of rats with 4 day ovarian cycles are found to have ovulated at the time of the poso-mortem examination. At an effective dose, aromatase inhibitors prevent ovulation ie. no eggs are found in the fallopian tubes.

In the above tests, the compounds of the formula I are active at less than 1µg/ml (in vitro) and less than 10mg/kg (in vivo), and the preferred compounds of the formula I are active at below 0.1 µg/ml (in vitro) and 0.5 mg/kg (in vivo).

Thus, according to a further feature of the invention there is provided a pharmaceutical or veterinary composition which comprises an effective amount of a compound of the formula I together with a pharmaceutically or veterinarily acceptable diluent or carrier.

The composition of the invention may be in a conventional pharmaceutical form suitable for oral administration, for example a tablet, a capsule, an emulsion or an aqueous or oily solution or suspension. The composition may contain conventional pharmaceutical excipients, and may be manufactured by conventional pharmaceutical techniques.

Preferred pharmaceutical or veterinary compositions of the invention are tablets and capsules containing from 1 to 100, preferably 5 to 50mg. of a compound of the invention.

According to a further feature of the invention there is provided the use of a heterocyclic compound of the formula I, wherein $R^1$ and $R^5$, which may be the same or different, are each a triazolyl, imidazolyl, pyridyl or pyrimidinyl radical; $R^2$, $R^3$ and $R^4$, which may be the same or different, are each a hydrogen atom or an alkyl, halogenoalkyl, alkoxy, cycloalkyl, or optionally substituted aryl, aryloxy or aralkyl radical; $R^6$ is a phenyl or naphthyl radical, optionally bearing one or more substituents selected from halogen atoms, amino, carboxamido, cyano and nitro radicals, and alkyl, halogenoalkyl, alkoxy, halogenoalkoxy, cycloalkyl, alkylamino, dialkylamino, alkoxycarbonyl, aryl, aryloxy and aralkyl radicals; and X is a direct bond, an alkylene, alkenylene or alkynylene radical, or an oxyalkylene or thioalkylene radical wherein respectively the oxygen or sulphur atom is bonded to $R^6$, for the manufacture of a pharmaceutical or veterinary composition having aromatase inhibitory activity.

Preferred heterocyclic compounds of the formula I for such use are those wherein $R^1$ and $R^5$ are each a triazolyl radical, particularly a 1,2,4-triazol-1-yl radical, X is a direct bond, $R^2$ and $R^3$ are each a hydrogen atom, $R^4$ is a 1-6C alkyl radical, especially a methyl or ethyl radical, and $R^6$ is a phenyl or naphthyl radical, optionally substituted as defined above, particularly a phenyl radical bearing one or two substituents selected from halogen, especially chlorine and fluorine, and trifluoromethyl.

The compounds of the invention also possess antifungal properties which are useful in combatting a wide variety of plant fungal diseases.

The compounds can move acropetally when applied to the plant tissue, and can also be volatile enough to be active in the vapour phase against fungi on the plant.

The compounds may be used as such for plant fungicidal purposes but are more conveniently formulated into compositions for such usage. The invention thus provides also a plant fungicidal composition comprising a compound of general formula I and a nonpharmaceutical carrier or diluent.

The invention also provides a method of combatting fungal diseases in a plant, which method comprises applying to the plant, to seed of the plant or to the locus of the plant or seed a compound of the formula I.

The compound can be applied in a number of ways, for example it can be applied, formulated or unformulated, directly to the foliage of a plant, to seeds or to the medium in which plants are growing or are to be planted, or it can be sprayed on, dusted on or applied as a cream or paste formulation, or it can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged, and the choice of a suitable conventional composition, and the method by which such a composition may be manufactured, are apparent to those skilled in the art.

The plant fungicidal compositions of this invention can comprise also other compound(s) having biological activity, e.g. compounds having similar or complementary fungicidal activity or compounds having plant growth regulating, herbicidal or insecticidal activity.

The invention is illustrated but not limited by the following Examples. Temperatures given are in degrees Celsius:

EXAMPLE 1

A mixture of 4-chloro-α-phenoxy-α-(1,2,4-triazol-1yl)acetophenone (6.25g), trimethyl-sulphoxonium iodide (4.4g), potassium hydroxide (1.15g) and 1,2,4 triazole (1.4g) in tert-butyl alcohol (150ml) was heated at 80° for 8 hours, then cooled and partitioned between ethyl acetate and water. The organic phase was separated, washed with water, then brine, dried ($Na_2SO_4$) and evaporated to dryness under reduced pressure. The residue was part purified on a silica column eluting with 98/2 v/v chloroform-methanol, followed by rechromatography on a "Lobar" silica column using ethyl acetate as eluent to give a less polar diastereoisomer with m.p. 129-131° 131o and a more polar diastereoisomer with m.p 185-187°, of 2(4-chlorophenyl)-1phenoxy-1,3-di (1,2,4 triazol-1-yl)propan-2ol.

The 4-chloro-α-phenoxy-α-(1,2,4 triazol-1-yl)acetophenone, used as starting material in the above process was obtained as follows:

Bromine (11.6g) in chloroform (40ml) was added dropwise to a stirred solution of 4-chloro-α-phenoxyacetophenone (18.8g) in chloroform (1200ml) containing dibenzoyl peroxide (50 mg) under photoflood illumination. The reaction was complete after 2 hours, and the chloroform was removed under reduced pressure to give α-bromo-4-chloro-α-phenoxyacetophenone which was used without further purification.

The α-bromo-4-chloro-α-phenoxyacetophenone (25.1g) was dissolved in acetonitrile (200ml). Potassium carbonate (25g) and 1,2,4 triazole (5.15g) were added and the suspension was stirred at ambient temperature for 18 hours. The reaction was poured into water and extracted with ethyl acetate. The extract was washed with water, then washed with brine, dried, and evaporated to dryness under reduced pressure. The residue was purified by medium pressure liquid chromatography (mplc) on a silica column, eluting with chloroform to give the α-bromo-4-chloro-α-phenoxyacetophenone as a gum; nmr in deuteriochloroform: 8.42(s,1H), 7.98(s,1H), 7.95(d,2H), 7.45(d,2H), 6.6(s,1H), 3.7(m,2H), 1.2(t,1H).

EXAMPLE 2

In a similar manner there was prepared 2-(4-chlorophenyl)-1-(2,4-difluorophenoxy)1,3-di(1,2,4-triazol-triazol-1-yl)propan-2 ol, mp 105-107° (less polar diastereoisomer) and 75-78° (more polar diastereoisomer), via the intermediate 4-chloro-α-(2,4difluorophenoxy)-α-(1,2,4-triazol-1-yl)acetophenone, m.p. 140-142°.

EXAMPLE 3

A mixture of 2-fluoro-α(4-fluorobenzyl)-α-(1,2,4-triazol-1yl)4-trifluoromethylacetophenone (1.0 g), trimethylsulphoxonium iodide (0.63g), potassium hydroxide (0.3g) and 1,2,4-triazole (0..3g) in tert-butyl alcohol (10ml) was heated at 70° for 18 hours, then cooled, poured into water and extracted with ethyl acetate. The ethyl acetate was separated, washed with water, dried and evaporated to dryness under reduced pressure. The residue was purified on a silica column, eluting with 2% v/v methanol/dichloromethane to give the more polar diastereoisomer of 1-(4-fluorobenzyl)2-(2-fluoro-4-trifluoromethylacetophenone,-1,3- di(1,2,4-triazol-1-yl )propan-2ol, m.p. 130–132°, and the less polar diastereoisomer with m.p. 131–133°.

The 2-fluoro-α-(4-fluorobenzyl)-α-(1,2,4-triazol-1-yl)-4-trifluoromethylacetophenone, used as starting material in the above process, was obtained as follows:

2-Fluoro-4-trifluoromethylacetophenone (5.0g) was added during 30 minutes to a solution of sodium hydroxide (1.0g) in 20%v/v ethanol/water (20ml) under water bath cooling and then stirred for a further 30 minutes. 4-Fluorobenzaldehyde was then added and the reaction was stirred overnight. The reaction was cooled and filtered to give the 3-(4-fluorophenyl)1-(2-fluoro-4-trifluoromethylphenyl)2-propenone with m.p. 77–78°.

The propenone (6.0 g) was dissolved in ethanol (60ml) and was reduced with hydrogen over 5% Pd on charcoal catalyst (0.6g) over 6 hours. The reaction was filtered through kieselguhr (Celite), and concentrated under reduced pressure to give the 2-fluoro-α-4-fluorobenzyl-4-trifluoromethylacetophenone as a gum.

Bromine (1.5g) in chloroform (5ml) was added dropwise to a stirred solution of 2 fluoro-α-4-fluorobenzyl)-4-trifluoromethylacetophenone (3.0g) in chloroform (20ml) during 6 hours. The mixture was stirred for 16 hours, then poured into water (100ml). The organic phase was separated, dried and evaporated to dryness to give α-bromo-2-fluoro-α-(4-fluorobenzyl)4-trifluoromethylacetophenone as an oil which was used without further purification.

The α-bromoacetophenone (4g) was dissolved in acetonitrile (5ml), sodium 1,2,4 triazole (1.0g) was added and the suspension was stirred for 16 hours. The reaction was filtered through kieselguhr (Celite), then poured into water and extracted with ethyl acetate. The extract was washed with water and brine, dried and evaporated to dryness under reduced pressure. The residue was purified on a silica column, eluting with 50% v/v ethyl acetate/petroleum ether (b.p.60–80C), then by recrystallisation from ethyl acetate/hexane to give the required acetophenone starting material.

EXAMPLE 4

A mixture of α-phenyl-α-(1,2,4-triazol-1-yl)4-trifluoromethylacetophenone (6.0g), trimethyl-sulphoxonium iodide (4.4g), potassium hydroxide (1.5g) and 1,2,4 triazole (1.4g) in tert-butyl alcohol (50ml) was heated at 70° for 18 hours, then cooled, poured into water and extracted with ethyl acetate. The ethyl acetate was separated, washed with water and then brine, dried and evaporated to dryness under reduced pressure. The residue was purified on a silica column, eluting with 10% v/v methanol/chloroform to give the more polar diastereoisomer of 1-phenyl-1,3-di(1,2,4-triazol-1-yl)-2-(4-trifluoromethylphenyl)2-ol m.p. 288–289°, and the less polar diastereoisomer with m.p. 123–125°.

The α-phenyl-α(1,2,4-triazol-1-yl)4-trifluoromethyl-acetophenone, used as starting material in the above process, was obtained as follows:

Bromine (17g) in ether (100ml) was added dropwise to a stirred solution of α-phenyl-4-trifluoromethylacetophenone (17.0 g) in chloroform (125ml) under photoflood lamp illumination during 90 minutes. The mixture was stirred for 45 minutes, then poured into water (100ml). The organic phase was separated dried and evaporated to dryness to give α-bromo-α-phenyl-4-trifluoromethylacetophenone, as an oil which is used without further purification.

The α-bromoacetophenone (22g) was dissolved in acetonitrile (100ml), sodium 1,2,4 triazole (6.3g) was added and the suspension was stirred for 48 hours, then poured into water and extracted with ethyl acetate. The extract was washed with water and brine, dried and evaporated to dryness under reduced pressure. The residue was purified on a silica column, eluting with 80% v/v ethyl acetate petroleum ether (b.p. 60–80C), then by recrystallisation from ethyl acetate/hexane to give the required acetophenone starting material.

EXAMPLE 5

2-(4-Chlorobenzyl)1,3-bis(1,2,4-triazol-1-yl)2-propanol (0.318g) was added to a solution of diethylamino sulphur trifluoride (0.128g) in chloroform (15ml), and the resulting yellow solution was stirred at room temperature for 3.5 hr. The mixture was then poured into water and the organic layer was separated, washed with water, dried, and evaporated to dryness. The yellow oil so obtained was purified by chromatography on a 25cm silica (Merck "Lobar") column, eluting with 3% v/v methanol in chloroform, to give a colourless oil which was crystallised from diethyl ether to give 2-(4-chlorobenzyl)-2-fluoro-1,3-bis(1,2,4-triazol-1-yl) propane, m.p. 161–163°.

EXAMPLES 6–9

The process described in Example 1, using the appropriate α-substituted substituted acetophenone starting material, to prepare:

2-(4-chlorophenyl)1-(4-fluorophenoxy)-1,3-di(1,2,4-triazol-1-yl)propan-2-ol, mp. (less polar diastereoisomer)161–162°(Example 6,(more polar diastereoisomer)152 –153°, (Example 7);

2-(4-chlorophenyl)1-methoxy-1,3-di(1,2,4-triazol-1-yl)propan-2-ol, more polar diastereoisomer identified by NMR in deuteriochloroform: δ 6 3.4(3H,s); 4.7(2H,q); 5.7(1H,s); 7.15(4H,dd); 7.75(1H,s); 7.8(1H,s); 7.85(1H,s); 8.18(1H,s); (Example 8);

2-(4-chlorophenyl)1-isopropoxy-1,3 di(1,2,4 -triazol-1-yl(propan-2-ol, more polar diastereoisomer identified by NMR in deuteriochloroform: 6 1.05(3H,d); 1.25(3H,d); 3.72(1H,m); 4.75(2H,q); 5.85(1H,s); 7.25(4H,q); 7.78(1H,s); 7.85(1H,s); 7.9(lH,s); 8.25(lH,s), (Example 9).

The acetophenone starting materials were obtained as described in the latter part of Example 1, and characterised as follows:

Starting material for Examples 6 and 7, mp 78–80°

Starting material for Example 8; NMR in deuteriochloroform: 3.55(3H,s), 6.55(1H,s), 7.5(2H,d), 7.95(2H,d), 8.02(lH,s), 8.43(1H,s).

Starting material for Example 9; NMR in deuteriochloroform: 6 1.1(3H,d), 1.32(3H,d), 3.85(1H,m), 6.67(1H,s), 7.42(2H,d), 7.90(2H,d), 7.92(1H,s), 8.4(1H,s).

EXAMPLES 10–17

The process described in Example 3 was repeated, using the appropriate acetophenone starting material, to give the following compounds:

1-Benzyl-2-(2,4 difluorophenyl)-1,3-di(1,2,4 -triazol-1-yl(propan2-ol;

more polar diastereoisomer mp 85–87° (Example 10).

less polar diastereoisomer mp 111–113° (Example 11).

1-(4-trifluoromethylbenzyl)-2-(2,4-difluorophenyl)-1,3-di(1,2,4-triazol-1-triazol-1-yl) propan-2ol;

more polar diastereoisomer mp 177–178° (Example 12)

less polar diastereoisomer mp 98° (Example 13)

1-(4-ethylbenzyl)-2-(2,4-difluorophenyl)1,3di(1,2,4 triazol-1-yl)propan2-ol;

more polar diastereoisomer mp 143–144° (Example 14)

less polar diastereoisomer mp 210–211° (Example 15)

1-(4 cyanobenzyl)-2-(2,4-difluorophenyl)1,3-di(1,2,4-triazol-1-yl)propan2-ol;

more polar diastereoisomer mp 172–173° (Example 16)

less polar diastereoisomer mp 134–135° (Example 17)

The acetophenone starting materials used in the above process were obtained from the reaction of 1-(2,4-difluorophenyl)-3-(1,2,4-triazol-1-yl)propan-2-one with the appropriate benzyl halide, by the process described generally in European Patent Specification No. 0 153 803, and have the following characteristics:

| Starting acetophenone for Example | Mp |
|---|---|
| 10, 11 | (a) |
| 12, 13 | 71–72 |
| 14, 15 | 93–94 |
| 16, 17 | 123–124 |

(a)NMR in deutericochloroform: δ 3.5(2H,m), 5.9(1H,m), 6.7–7.3(8H,m), 7.85(1H,s), 7.95(1H,s).

EXAMPLE 18 The process described in Example 4 was repeated, using 4-chloro-α-phenyl-α-(1,2,4-triazol-1-yl)acetophenone as the starting material, to give the more polar diastereoisomer of 2-(4-chlorophenyl)-1-phenyl-1,3-di(1,2,4-triazol-1-yl)propan-2ol, mp 118–119°.

EXAMPLES 19–20

The process described in Example 5 was repeated, using the appropriate 2-propanol starting materials, to obtain:

2-fluoro-2-(2-fluoro-4-chlorobenzyl)1,3-di(1,2,4-triazol-1-yl)propane, mp 169–170° (Example 19);

2-fluoro-2-(2-fluoro-4-trifluoromethylbenzyl)1,3-di(1,2,4-triazol-1-yl)propane, mp 133–135° (Example 20).

EXAMPLES 21–22

The Grignard agent formed from 4-chlorophenethyl bromide was treated with a solution of 1,3-dichloroacetone in diethyl ether, and then with a solution of sodium triazole in dimethylformamide, by the process described generally in European Patent Specification No. 0250198, to give:

2-(4-chlorophenethyl)1,3-di(1,2,4-triazol-1-yl)propan-2-ol, NMR in deuteriochloroform: 6 3.6(2H,s); 4.45(4H,q); 6.75(2H,d); 7.25(2H,d); 7.95(2H,s); 8.2(2H,s), (Example 21); In a similar manner, starting from 4 chlorophenylpropyl bromide, there was obtained 2 (4 chlorophenylpropyl) 1,3-ii(1,2,4 triazol-1-yl)propan-2-il, mp 152–154°, (Example 22).

EXAMPLE 23

A mixture of 1-(4-chlorophenoxy)3-(1,2,4-triazol-1-yl)propan-2-one (0.7g), trimethylsulphoxonium iodide (0.74g), potassium hydroxide (0.38g) and 1,2,4-triazole (0.23g) in tert butyl alcohol (15ml) was heated at 80° for 2.5h, then cooled and partitioned between ethyl acetate and water. The organic phase was separated, washed with water and then brine, dried and evaporated to dryness under reduced pressure. The residue was purified by chromatography on a Lobar silica column, using 2% methanol in chloroform as eluent, to give 2(4-chlorophenoxymethyl)1,3-di(1,2,4-triazol-1-yl)propan-2-ol as a gum. NMR in deuteriochloroform: δ 3.6(2H,s); 4.45(4H,q); 6.75(2H,d); 7.21(2H,d); 7.95(2H,s); 8.2(2H,s).

The 1-(4-chlorophenoxy)3-(1,2,4-triazol-1-yl)propan-2-one used as starting material in the above process was obtained as follows:

A mixture of 2-(4-chlorophenoxy)oxirane (18.4g), potassium carbonate (13.8g) and 1,2,4 triazole (13.8g) in acetonitrile (130ml) was stirred at room temperature for 48 h. The acetonitrile was removed by concentration under reduced pressure, and the residue was partitioned between ethyl acetate and water. The organic phase was separated, washed with water, dried and evaporated to dryness under reduced pressure. The residual yellow oil was purified by silica column chromatography, using 5% by volume methanol in chloroform as eluent, to give 1-(4-chlorophenoxy)-3-(1,2,4--triazol-1-yl)propan-2 ol) as a white solid, which was used without further purification.

The 1-(4-chlorophenoxy) 3-(1,2,4-triazol-1-yl)propan-2 ol (3.0g) was dissolved in acetone (100ml) and treated with Jones reagent (3ml) for 3 h. To complete the oxidation, two subsequent additions of Jones reagent (0.5ml) were added. After cooling, ethyl acetate (150ml) was added and the reaction was neutralised by the addition of a saturated solution of sodium bicarbonate. The organic phase was separated, washed with water, dried and concentrated to dryness under reduced pressure. The residue was purified by chromatography on silica using 2% by volume methenol in chloroform as eluent, to give 1-(4-chlorophenoxy)-3-(1,2,4-triazol -1-yl)propan-2-one as a gum, NMR in deuteriochloroform: δ4.7(2H,s), 5.38(2H,s), 6.85(2H,d), 7.3(2H,d), 8.01(1H,s), 8.17(1H,s).

EXAMPLE 24

A mixture of 3-(4-chlorophenyl)1-(1,2,4-triazol-1-yl)butan-2-one (0.7g), trimethylsulphoxonium iodide (0.77g), potassium hydroxide (0.38g) and 1,2,4-triazole (0.24g) in tert butyl alcohol (l0ml) was heated at reflux for 4h. The reaction mixture was cooled and poured into water, and the aqueous phase was separated and extracted with ethyl acetate. The organic extract was separated, dried and concentrated to dryness under reduced pressure, and the residue was purified by column chromatography on silica using 2% by volume methanol in chloroform as eluent, to give 3 (4 chlorophenyl)-1-(1,2,4-triazol-1-yl)-2(1,2,4-triazol-1-ylmethyl)butan-2-ol mp 60–64° .

The butan-2-one used as starting material in the above process was obtained as follows:

Sodium hydride (0.192g, 55% suspension in oil) was added portion wise to a stirred solution of 1-(4-chlorophenyl)-3(1,2,4-triazol-1-yl)propan-2-one (0.94g) in anhydrous dimethylformamide (10ml) at 5°C. When hydrogen evolution had ceased, methyl iodide (0.62g) was added, the resultant solution allowed to reach room temperature and then stirred for 4 ½h. The reaction mixture was partitioned between ethyl acetate and water, the organic phase was separated, washed with water, then brine, dried and evaporated to dryness under reduced pressure. The residue was purified by chromatography in silica, using 2% by volume methanol in chloroform as eluent, to give 1-(4-chorophenyl)1-methyl-3-(1,2,4-triazol-1-yl(propan-2-one as a colourless oil, NMR in deuteriochloroform: δ 1.4(3H,d); 3.83(1H,q); 4.95(2H,s); 7.2(4H,q); 7.95(2H,s).

EXAMPLES 25-26

The process described in Example 24 was repeated, using the appropriate substituted ketone as starting material, to give:

3-(4-chlorophenyl)1-(1,2,4-triazol-1-yl)2-(1,2,4-triazol-1-ylmethyl)-4-(4-trifluoromethylphenyl)butan-2-ol, mp 145–147° (Example 25);

4[2-(4-chlorophenyl)-3-hydroxy-4-(1,2,4-triazol-1-yl)-3-(1,2,4-triazol-1-ylmethyl)butyl]benzonitrile, mp 85–87° (Example 26).

The required ketone starting materials were obtained by the process described in the latter part of Example 24, using an appropriate benzyl halide in place of methyl iodide.

EXAMPLE 27

A mixture of 2-(4-chloro-α-fluorobenzyl)-2-(1,2,4-triazol-1-ylmethyl)oxirane (140mg), potassium carbonate (72mg) and 1,2,4-triazole (52 mg) in acetonitrile (10ml) was heated at 40° for 2h, then evaporated to dryness under reduced pressure. The residue was partitioned between ethyl acetate and water, and the organic phase was separated, washed with water and brine, dried and evaporated to dryness. The residue was purified by chromatography on silica, using 1% by volume methanol in chloroform as eluent, to give after trituration with a mixture of ethyl acetate and hexane, 2-(4-chloro-α-fluorobenzyl)-1,3-di(1,2,4-triazol-1yl) propan-2ol, mp 144 –145°.

The 2-(4-chloro-α-fluorobenzyl)-2-(1,2,4-triazol-1ylmethyl)oxirane used as starting material in the above process, was obtained as follows:

3-Chloroperbenzoic acid (54g) was added to a solution of 4-chloroocinnamyl chloride (J. Pharm. Soc., 1973, 62 911; 65g) in chloroform (200ml) and the mixture was stirred for 20h. The reaction mixture was filtered and the organic layer was washed with saturated sodium bicarbonate solution, then brine, and dried. Concentration under reduced pressure gave 2-(4-chlorophenyl)-3-chloromethyloxirane as a colourless oil. NMR in deuteriochloroform: δ3.25(1H,m), 3.7(2H,d), 3.8(1H,d), 7.18(2H,d), 7.28(2H,d).

Hydrogen fluoride-pyridine complex (60ml) was added under argon via a syringe, to a solution of the above oxirane (30g) in anhydrous tetrahydrofuran (200ml) at 5–10°, and then stirred overnight. The reaction mixture was poured into saturate sodium carbonate solution and extracted with diethyl ether. The ether extract was washed with water and brine, dried and evaporated to dryness under reduced pressure. The residue was purified by chromatography on silica, using diethyl ether:hexane 1:1 by volume, an eluent, to give 3-chloro-1-(4-chlorophenyl)-1-fluoropropan-2ol as a pale yellow oil, which was used without further characterisation.

Sodium triazole (7g) was added to a solution of 3-chloro-1-(4-chlorophenyl)-1-fluoropropan-2-ol (14g) in anhydrous dimethyl formamide (150ml) and the reaction mixture was heated at 100° for 2h. The reaction mixture was then partitioned between ethyl acetate and water, and the organic phase was washed with water and brine, and dried. After evaporation to dryness under reduced pressure, the residue was purified by chromatography on silica using 5% by volume methanol in chloroform as the eluent, to give 1-(4 chlorobenzyl) 1-fluoro-3-(1,2,4-triazol-1-yl)propan propan-2-ol, mp 124–125°.

To a solution of the propanol (250mg) in acetone (50ml) at −10° Jones reagent (20mls: prepared from chromium trioxide sulphuric acid), and the reaction mixture was stirred for 16h, poured into ethyl acetate and basified with saturated sodium bicarbonate solution. The organic phase was separated, washed with water and brine and dried. The solvent was evaporated under reduced pressure and the residue was purified by chromatography on silica, using 5% by volume methanol in chloroform as eluent, to give 1-(4-chlorophenyl)1-fluoro3-(1,2,4-triazol-1-yl)propan propan-2-one mp 106–107 °.

A solution of 1-(4-chlorophenyl-1-fluoro-3 (1,2,4-triazol-1-yl(propan-2-one (250mg) in dimethyl sulphoxide (5ml) was added under argon to a mixture of trimethylsulphoxonium iodide (430mg) and dimsyl sodium (formed from dimethyl sulphoxide (5 ml) and sodium hydride (38 mg). The reaction mixture was stirred for 20 h, and partitioned between ethyl acetate and water and the organic phase separated, washed with water, then brine and dried. The dried extract was concentrated to dryness under reduced pressure, and the residue was chromatographed on silica using chloroform.

EXAMPLE 28

10% Palladium on charcoal (200 mg) was added under argon to a solution of 1-(4-chlorophenyl)-3-(1,2,4-triazol-1-yl)-2-(1,2,4-triazol-1-ylmethyl)propene (750 mg) in absolute ethanol (50 ml). After uptake of the theoretical amount of hydrogen, the reaction mixture was filtered through Kieselguhr ( Celite— trademark) and evaporated to dryness under reduced pressure. The residual oil was purified by chromatography on silica, using chloroform as eluent, and after evaporation of the solvent, the residue was treated with ethereal hydrogen chloride to give 2-(4-chlorobenzyl)1,3-bis(1,2,4-triazol-1-yl)propane: m.p. 107 –108 °.

The 1-(4-chlorophenyl)3-(1,2,4-triazol-1-yl)-2(1,2,4-triazol-1-ylmethyl)propene used as starting material in the above process was obtained as follows:

A mixture of 2-(4-chlorobenzyl)1,3-di(1,2,4-triazol1-yl)propan-2-ol (1.0g), imidazole (1.1g), thionyl chloride (1ml) in acetonitrile (50 ml) was heated at 60° for 90 minutes. The reaction was cooled, poured into water and extracted into ethyl acetate. The organic phase was separated, washed with water, then saturated sodium bicarbonate solution and then brine, and dried. The dried extract was evaporated to dryness under reduced pressure, and the residue was purified by chromatography on silica, using 2% by volume, methanol in chloroform as eluent to give the required starting material, mp. 86–87° .

EXAMPLE 29

Sodium hydride (0.036 g) was added to a stirred solution of 2-(4-chlorobenzyl)-1,3-bis(1,2,4-triazol-1-yl)propan-2-ol (0.48 g) in dry dimethylformamide, and the reaction mixture was stirred until hydrogen evolution ceased. α-Bromo-p-toluonitrile (0.44 g) was then added and the mixture was stirred for 18 h at room temperature. The reaction mixture was poured into water and extracted with ethyl acetate. The organic extract was washed with water, dried and evaporated to dryness under reduced pressure to a sticky white solid. The residue was purified by chromatography on silica using 5% by volume methanol in chloroform as eluent, and after evaporation of the solvent the residual gum crystallised from a mixture of diethyl ether and hexane to give 4-[2-(4-chlorophenyl)-1,3-di(1,2,4-triazol-1-ylmethyl)ethoxymethyl]benzonitrile, m.p. 173–175°C.

EXAMPLE 30

1-(4-trifluoromethylphenyl)-3-(1,2,4,-triazol-1-yl)propan-2-one (1.5 g), trimethylsulphoxonium iodide (1.5 g), imidazole (0.46 g), potassium carbonate (0.75 g) in tert-butyl alcohol (20 ml) was heated at $\phi°$ for 3 h. The reaction mixture was partitioned between ethyl acetate and water, and the organic layer was separated, washed with water and then brine, and dried. The dried extract was evaporated to dryness under reduced pressure, and the residue was purified by chromatography on silica, using 5% by volume methanol in chloroform as eluent. After evaporation of the solvent, the residue crystallised from a mixture of ethyl acetate and hexane to give 3-(imidazol-1-yl)1-(1,2,4-triazol-1-yl)-2(4-trifluoromethylbenzyl)-propan-2-ol, m.p. 154–155°C. (Example 30). In a similar manner there were prepared 2-(4-chlorobenzyl)-3-(imidazol-1yl)-1-(1,2,4-triazol-1-yl) propan-2-ol, m.p. 159–161° (Example 31) and 1,3-di(imidazol-1yl)-2-(4-trifluoromethylbenzyl)propan-2-ol, m.p. 177–178° (Example 32).

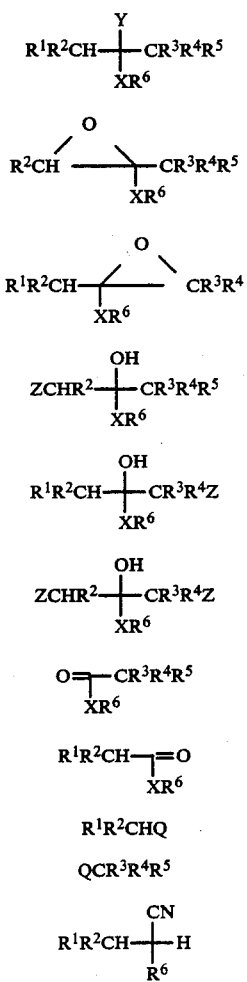

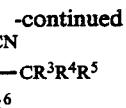

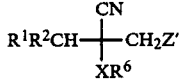

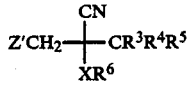

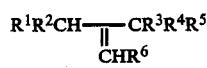

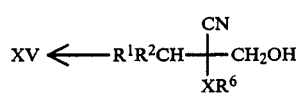

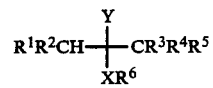

I claim:

1. A heterocyclic compound of the formula I:

$$R^1R^2CH \underset{XR^6}{\overset{Y}{-}} CR^3R^4R^5$$

wherein $R^1$ is a triazolyl radical, $R^5$ is a triazolyl radical; $R^2$, $R^3$ and $R^4$, which may be the same or different, are each a hydrogen atom, a 1–6C alkyl, halogenoalkyl or alkoxy radical, a 3–8C cycloalkyl radical, or a phenyl, naphthyl, phenoxy, naphthyloxy or phenyl(1–6C alkyl) radical, in each of which the aryl group optionally bears one or more substituents selected from the group consistiong of halogen atoms, amino, carboxyamido, cyano and nitro radicals, 1–6C alkyl, halogenoalkyl, alkoxy, halogenoalkoxy and alkylamino radicals, 3–8C cycloalkyl radicals, di(1–6C alkyl)amino radicals and 2–6C alkoxycarbonyl radicals; $R^6$ pl is a phenyl or naphthyl radical optionally bearing one or more substituents as definded above; X is a direct bond, a 1–4C alkylene radical, a 2–4C alkenylene or alkynylene radical, or a 1–4C oxyalkylene or thioalkylene radical wherein respectivly the oxygen or sulphur atom is bonded to $R^6$ or a phenyl(2–4C)alkenylene radical in which the phenyl group bears one or more substituents as defined above for $R^6$; and Y is a halogen atom, and provided that when X is a direct bond, Y is not halogen; and when the compound contains a basic nitrogen atom, pharmaceutically acceptable acid addition salts thereof.

2. A heterocyclic compounds as claimed in claim 1 wherein $R^1$ and $R^5$ are a 1,2,4-triazol-1-yl, radical; $R^2$, $R^3$ and $R^4$, which may be the same or different, are each a hydrogen atom or a methyl, ethyl, propyl, isopropyl, butyl, pentyl, hexyl, trichloromethyl, difluoromethyl, trifluoromethyl, 1— or 2-chloroethyl, 2,2,2-trichloroethyl, 1-or 2-fluoroehtyl, 1,1-, 1,2-or 2,2-difluoroethyl, 1,1,2-, 1,2,2- or 2,2,2-trifluoroethyl, 2,2,3,3,3-pentafluoropropyl, methoxy, ethoxy, propoxy, isopropoxy, butoxy, pentyloxy, hexyloxy, cyclopropyl, cyclopentyl, cyclohexyl or cyclooctyl radical, or a phenyl, naphthyl, phenoxy, naphthyloxy, 3 phenylpropyl, 6 phenylhexyl, 1- or benzyl, phenethyl, 1-phenylethyl, 2 naphthylmethyl, 1-or 2 (1- or 2 naphthyl)ethyl or 6 (1-or 2 naphthyl)hexyl radical, in each of which the aryl group optionally bears one or more substituents selected from fluorine, chlorine and bromine atoms, and amino, carbamoyl, carboxamido, cyano, nitro, methyl, ethyl, propyl, isopropyl, butyl, isobutyl, sec-butyl, tert-butyl, pentyl, hexyl, trichloromethyl, difluoromethyl, trifluoromethyl, 1- or 2-chloroethyl, 2,2,2-trichloroethyl, 1- or 2-fluoroethyl, isopropoxy, butoxy, pentyloxy, hexyloxy, trifluoromethoxy, 2,2,2 trichloroethoxy, 1,1 , 1,Z- and 2,2-difluoroethoxy, 1,1,2 , 1,2,2 and 3 tetrafluoropropoxy, 2,2,2 trifluoroethoxy, pentafluoroethoxy, 2,2,3, thylamino, ethylamino, hexylamino, cyclopropyl, cyclopentyl, cyclohexyl, cyclooctyl, dimethylamino, diethylamino, ethylmethylamino, dipropylamino, dihexylamino, methoxycarbonyl, ethoxycarbonyl, propoxycarbonyl and hexyloxycarbonyl radicals; R6 is a phenyl or naphthyl radical optionally bearing one or more substituents as defined above; X is a methylene, ethylene, ethylidene, propylidene, butylidene, trimethylene, tetramethylene, 1-or 2 methylethylene, 1- or 2 ethylethylene, 1-, 2 or 3 methyltrimethylene, 2 methylpropylidene, vinylene, ethynylene, oxymethylene or thiomethylene radical, or a benzylidene radical, in which the phenyl ring optionally bears ohe or more substituents as defined above; and Y is a fluorine, and the hydrochloride, nitrate, sulphate, phosphate, acetate, lactate, citrate, maleate and fumarate salts thereof.

3. A compound as claimed in claim 1 wherein $R^5$ is a 1,2,4 triazolyl radical; $R^2$, $R^3$ and $R^4$ are all hydrogen atoms; X is a methylene, fluoromethylene or ethylidene radical; Y is a fluorine atom; and $R^6$ is a phenyl radical bearing one or two substituents selected from the group consisting of halogen atoms and trifluoromethyl radicals.

4. A compound as claimed in claim 3 wherein $R^6$ is a 4-chlorophenyl, 2-fluoro-4-chlorophenyl or 2-fluoro-4-trifluoromethyl phenyl radical.

5. A compound as claimed in claim 1 wherein I wherein $R^5$ is a 1,2,4-triazolyl radical; $R^2$ and $R^3$ are each a hydrogen atom; $R^4$ is a phenyl, phenoxy or benzyl radical optionally bearing a halogen or cyano substituent; and $R^6$ is a phenyl radical bearing one or two substituents selected from the group consisting of halogen atoms and trifluoromethyl radicals.

6. A compound as claimed in claim 5 wherein $R^4$ is a phenyl, 4-fluorophenoxy, 4-fluorobenzyl or 4-cyanobenzyl radical and $R^6$ is a 4-chlorophenyl, 2,4-difluorophenyl or 2-fluoro-4-trifluoromethyl phenyl radical.

7. A compound as claimed in claim 1 which is 2-(4-chlorobenzyl)-2-fluoro-1,3-di(1,2,4-triazol-1-yl)propane, 2-fluoro-2-(2-fluoro-4-chlorobenzyl)-1,3-di(1,24,4-triazol-1-yl)propane, 2-fluoro -(2-fluoro-4-chlorobenzyl)-1,3-di(1,2,4-triazol-1-yl)propane, 2-fluoro-2-(2-fluoro-4-trifluoromethylbenzyl)-1,3-di(1,2,4-triazol-1-yl)propane.

8. A pharmaceutical or veterinary composition which comprises an effective amount of a compound of the formula I as claimed in claim 1 together with a pharmaceutically or veterinarily acceptable diluent or carrier.

9. A method for the treatment of steroid hormone dependent diseases which comprises administering, to a host in need of such treatment, an effective amount of a heterocyclic compound of the formula I:

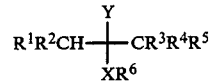

wherein $R^1$ is a triazolyl radical, $R^5$ is a triazolyl radical; $R^2$, $R^3$ and $R^4$, which may be the same or different, are each a hydrogen atom, a 1–6C alkyl, halogenoalkyl or alkoxy radical, a 3–8C cycloalkyl radical, or a phenyl, naphthyl, phenoxy, napthyloxy or phenyl(1–6C alkyl) radical, in each of which the aryl group optionally bears one or more substituents selected from the group consisting of halogen atoms, amino, carboxyamido, cyano and nitro radicals, 1–6C alkyl, halogenoalkyl, alkoxy, halogenoalkoxy and alkylamino radicals, 3–8C cycloalkyl radicals, di(1–6C alkyl)amino radicals and 2–6C alkoxycarbonyl radicals; $R^6$ is a phenyl or naphthyl radical optionally bearing one or more substituents as defined above; X is a direct bond, a 1–4C alkylene radical, a 2–4C alkenylene or alkynylene radical, or a 1–4C oxylkylene or thioalkylene radical wherein respectively the oxygen or sulphur atom is bonded to $R^6$ or a phenyl(2–4C)alkenylene radical in which the phenyl group bears one or more substituents as defined above for $R^6$; and Y is a hydrogen atom and when the compound contains a basic nitrogen atom, pharmaceutically acceptable acid addition salts thereof.

* * * * *